(12) United States Patent
Phillips

(10) Patent No.: US 9,696,294 B2
(45) Date of Patent: Jul. 4, 2017

(54) REMOVABLE TAMPER-RESISTANT BREATH ALCOHOL SAMPLING SYSTEM

(71) Applicant: Integrated Monitoring Systems, LLC, Lakewood, CO (US)

(72) Inventor: Brian K. Phillips, Lakewood, CO (US)

(73) Assignee: Integrated Monitoring Systems, LLC, Lakewood, CO (US)

( * ) Notice: Subject to any disclaimer, the term of this patent is extended or adjusted under 35 U.S.C. 154(b) by 48 days.

(21) Appl. No.: 14/729,361

(22) Filed: Jun. 3, 2015

(65) Prior Publication Data

US 2015/0362478 A1    Dec. 17, 2015

Related U.S. Application Data

(60) Provisional application No. 62/010,912, filed on Jun. 11, 2014.

(51) Int. Cl.
*G01N 33/497* (2006.01)
*A61B 5/08* (2006.01)

(52) U.S. Cl.
CPC ......... *G01N 33/4972* (2013.01); *A61B 5/082* (2013.01)

(58) Field of Classification Search
CPC ............................ G01N 33/4972; A61B 5/082
USPC ......................................................... 73/23.3
See application file for complete search history.

(56) References Cited

U.S. PATENT DOCUMENTS

| | | |
|---|---|---|
| 4,487,055 A | 12/1984 | Wolf |
| 4,678,057 A | 7/1987 | Elfman et al. |
| 4,707,336 A | 11/1987 | Jones |
| 4,736,619 A | 4/1988 | Legrand |
| 4,809,810 A | 3/1989 | Elfman et al. |
| 5,739,412 A | 4/1998 | Stock et al. |
| 6,479,019 B1 | 11/2002 | Goldstein |
| 6,923,040 B2 | 8/2005 | Stock |
| 6,967,581 B2 | 11/2005 | Karsten |
| 7,329,390 B2 | 2/2008 | Stock et al. |
| 8,773,239 B2 | 7/2014 | Phillips et al. |
| 2007/0144812 A1 | 6/2007 | Stewart |
| 2007/0167853 A1 | 7/2007 | Melker |
| 2007/0193335 A1* | 8/2007 | Son ...................... G01N 33/497 73/23.3 |
| 2008/0041652 A1 | 2/2008 | Kamiki |
| 2010/0241019 A1 | 9/2010 | Varga |
| 2011/0079073 A1* | 4/2011 | Keays .................. B60K 28/063 73/23.3 |

(Continued)

OTHER PUBLICATIONS

PCT Search Report and Written Opinion of the International Search Authority for International Application No. PCT/US2015/034901 dated Oct. 8, 2015, 8 pages.

*Primary Examiner* — Laura Martin
*Assistant Examiner* — Irving A Campbell
(74) *Attorney, Agent, or Firm* — Dorr, Carson & Birney PC

(57) ABSTRACT

A breath alcohol testing device has a removable tamper-resistant sampling chamber assembly that provides a disposable interface between the test subject and the alcohol sensor, other sensors and electronics of the testing device. Hydrophobic membranes prevent bodily fluids and other liquids from entering the alcohol sensor and other sensitive components of the testing device. A set of chambers with one-way valves direct the gas flow within the sample chamber assembly to ensure the breath sample delivered to the alcohol sensor is not diluted by the subject inhaling, and is a deep-lung breath sample.

11 Claims, 4 Drawing Sheets

(56) References Cited

U.S. PATENT DOCUMENTS

| | | | |
|---|---|---|---|
| 2012/0198910 A1* | 8/2012 | Lo | A61B 5/082 |
| | | | 73/23.3 |
| 2012/0330175 A1 | 12/2012 | Phillips et al. | |
| 2013/0021153 A1 | 1/2013 | Keays | |
| 2013/0120115 A1 | 5/2013 | Valls Chaparro | |
| 2013/0150727 A1 | 6/2013 | Phillips et al. | |
| 2013/0187757 A1 | 7/2013 | Phillips et al. | |
| 2013/0192338 A1* | 8/2013 | Mayer | G01N 33/4972 |
| | | | 73/23.3 |

* cited by examiner

REMOVABLE TAMPER-RESISTANT BREATH ALCOHOL SAMPLING SYSTEM

RELATED APPLICATION

The present application is based on and claims priority to the Applicant's U.S. Provisional Patent Application 62/010,912, entitled "Removable Tamper-Resistant Breath Alcohol Sampling System," filed on Jun. 11, 2014.

BACKGROUND OF THE INVENTION

Field of the Invention

The present invention relates generally to the field of breath alcohol testing devices. More specifically, the present invention discloses a removable tamper-resistant breath alcohol sampling system for use in a breath alcohol testing device.

Statement of the Problem

Breath alcohol testing systems have been widely used for many years. These systems typically require the test subject to exhale a breath sample into a mouthpiece attached to a sampling system and an alcohol sensor. The alcohol sensor can be an electrochemical fuel cell that oxidizes any alcohol present in the breath sample and outputs an electrical signal based on the amount of alcohol present in the sample. Many such systems rely on valves and precision pumps between the mouthpiece and the alcohol sensor to ensure that a predetermined sample volume flows into the alcohol sensor to allow accurate calibration of the testing system. The mouthpiece is typically disposable and is intended only for use with one test subject.

While these prior-art systems replace the mouthpiece from test subject to test subject, none replace the sampling system components where exhaled microbes can reside and potentially transmit disease from subject to subject. These systems are reliant on precise activation of sampling pumps to draw a predetermined volume of the exhaled breath sample into the fuel cell. Test subject inhalation during the sampling process could result in potential exposure to microbes contained in a prior test subject's exhaled breath. Another key shortcoming of the disposable mouthpiece is that it is difficult to obtain data on the characteristics of the breath sample exhaled by the subject, such as temperature, volume, and absolute pressure.

A variety of sampling systems been used as components in these breath alcohol testing units. For example, U.S. Pat. No. 4,707,336 (Jones) discloses a breath alcohol testing instrument having a removable mouthpiece attached to a gas sampling system containing an alcohol sensor and pressure sensor to measure breath alcohol content. The removable mouthpiece is intended to assist in preventing human fluid and disease transmission from subject to subject. No provision is made to replace sampling system components between test subjects other than the mouthpiece.

Many stationary breath alcohol testing devices utilize 10-12 inch long heated tubes attached to a sampling system and alcohol sensor. These heated tubes are a very positive environment for growth of microorganisms. The heated tube is intended stabilize the alcohol content in the breath sample by preventing condensation that can affect the alcohol content of the breath alcohol sample over such a long distance. The use of a pressure sensor attached to the mouthpiece has been known since the late 1980's to automate the sampling process, as shown for example in the Jones patent. While these approaches are helpful in minimizing disease transmission, these measures have limited effectiveness. The new class of remote alcohol monitoring devices requires that many tests are taken by a subject over a prolonged period of time (e.g., for six months to a year). The testing device is then returned to the monitoring organization and subsequently reassigned to a new test subject. The prolonged exposure of the testing device and sampling system to an individual who may have a contagious respiratory disease, or a disease that is passed in bodily fluids introduces a new level of disease transmission risk that may not be fully mitigated by a removable mouthpiece alone.

The alcohol sensor, other sensors and electronic components of a breath alcohol testing device are relatively expensive, so the entire testing device cannot be disposable. Therefore, a need exists for a breath alcohol testing device with a modular design combining disposable components (e.g., the mouthpiece and sample chamber) that can be replaced for each test subject, with permanent components (e.g., the alcohol sensor, other sensors and electronics). In addition, the sample chamber assembly protects the permanent components of the testing device from contact with bodily fluids or biological contamination.

In addition, there is always of the risk of tampering by the test subject in breath alcohol testing, particularly if the subject is attempting to circumvent the alcohol testing program. Tampering can lead to inaccurate test results as well as damaging the testing device. Thus, although authorized personnel must be able to readily disassemble the testing device for maintenance and repair, care must be taken to ensure that test subjects cannot easily tamper with the testing device.

Therefore, a need exists for a breath alcohol sampling system having a sampling system that can be readily removed by authorized personnel so that the testing device can be repaired and maintained, but that resists tampering by test subjects. In addition, the sampling system should shield the fuel cell and other components of the testing device from contact with bodily fluids or biological contamination.

Solution to the Problem

The present invention provides a sampling system for a breath alcohol testing unit that is tamper-resistant, but completely removable from the remainder of the breath alcohol testing unit. The present invention enables replacement of the components and surfaces exposed to potential disease-causing microorganisms and saliva mist. Bodily fluids are blocked from entering the alcohol sensor and sensor measurements systems, thereby preventing damage and subsequent transmission to new test subjects. In addition, the sample chamber is tamper-resistant due to a unique wire lock and locking sample chamber cap system.

SUMMARY OF THE INVENTION

This invention provides a removable tamper-resistant sampling chamber assembly for a breath alcohol testing device. The sampling chamber assembly provides a disposable interface between the test subject and the alcohol sensor, other sensors and electronics of the testing device. Hydrophobic membranes prevent bodily fluids and other liquids from entering the alcohol sensor and other sensitive components of the testing device. In addition, a set of chambers with one-way valves direct the gas flow within the sample chamber assembly to ensure the breath sample delivered to the alcohol sensor is not diluted by the subject inhaling, and is a deep-lung breath sample.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figure 1:
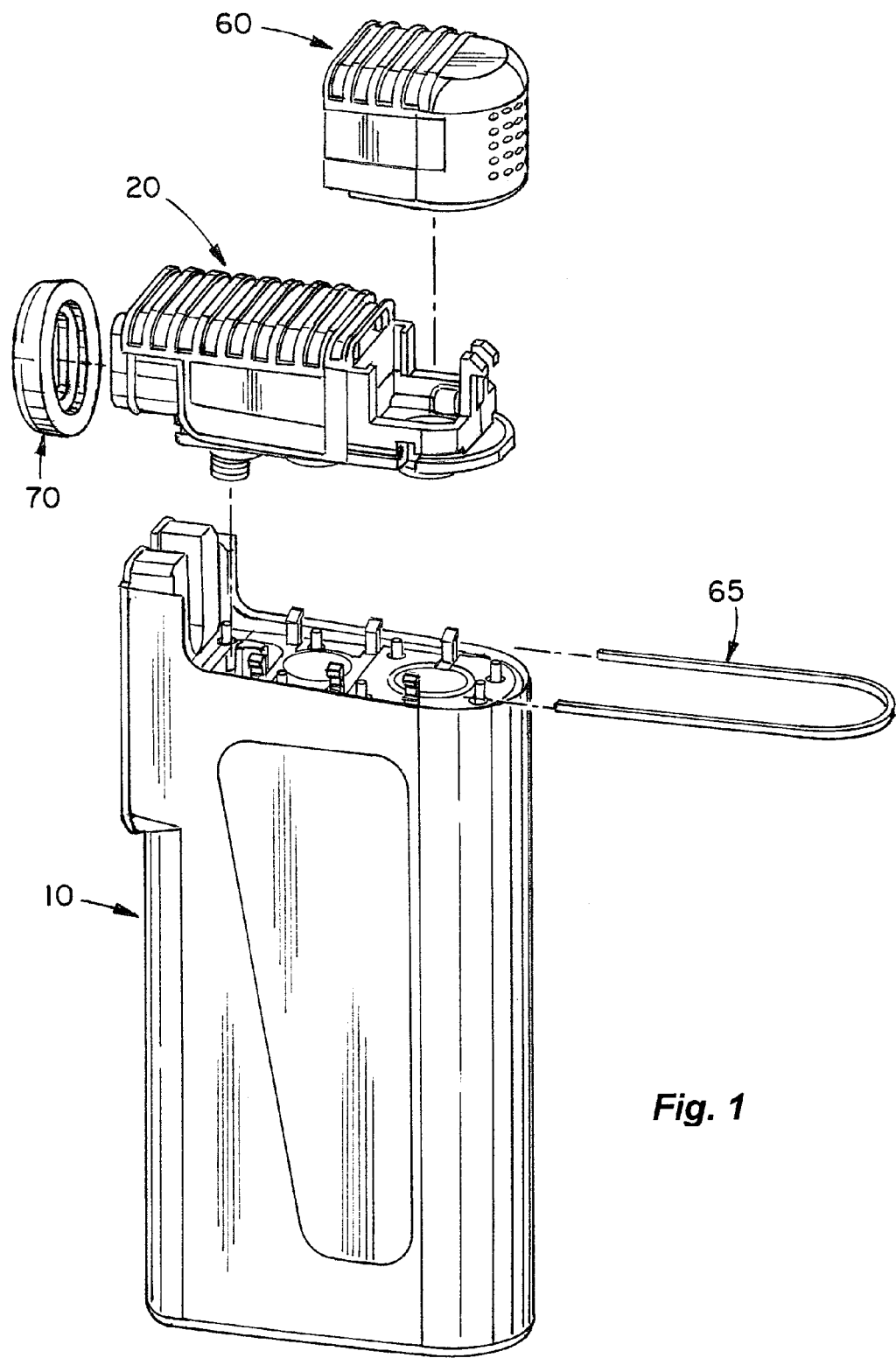
FIG. 1 is an exploded perspective view of a breath alcohol testing device 10 with a removable sample chamber assembly 20.
Figure 2:
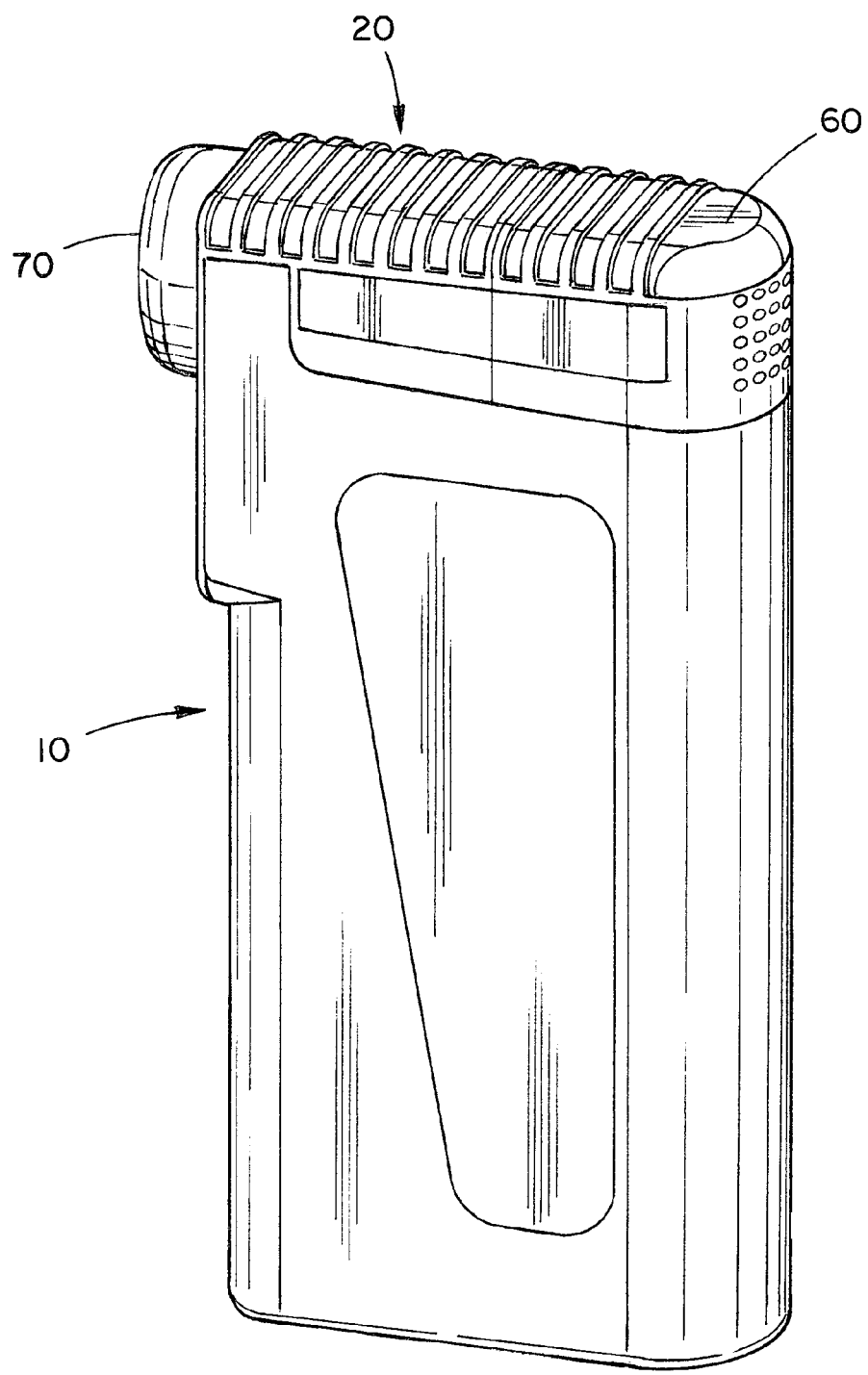
FIG. 2 is a perspective view of the assembled breath alcohol testing device 10 corresponding to FIG. 1.

FIGS. 1 and 2 are perspective views showing an embodiment of the present invention. As a general overview, the main housing of the breath alcohol testing device 10 contains the major non-disposable components of system, such as an alcohol sensor (e.g., a fuel cell), other sensors for biometric identification and test validation, and associated electronics. The sample chamber assembly 20, mouthpiece 70 and sample chamber cap 60 are disposable components that removably attach to the unit, as shown in FIG. 2, and are intended to be replaced for each test subject. The sample chamber assembly 20 includes an inlet port into which the test subject exhales, and controls the gas flow into and through a sample chamber used by the alcohol sensor.

Figure 3:
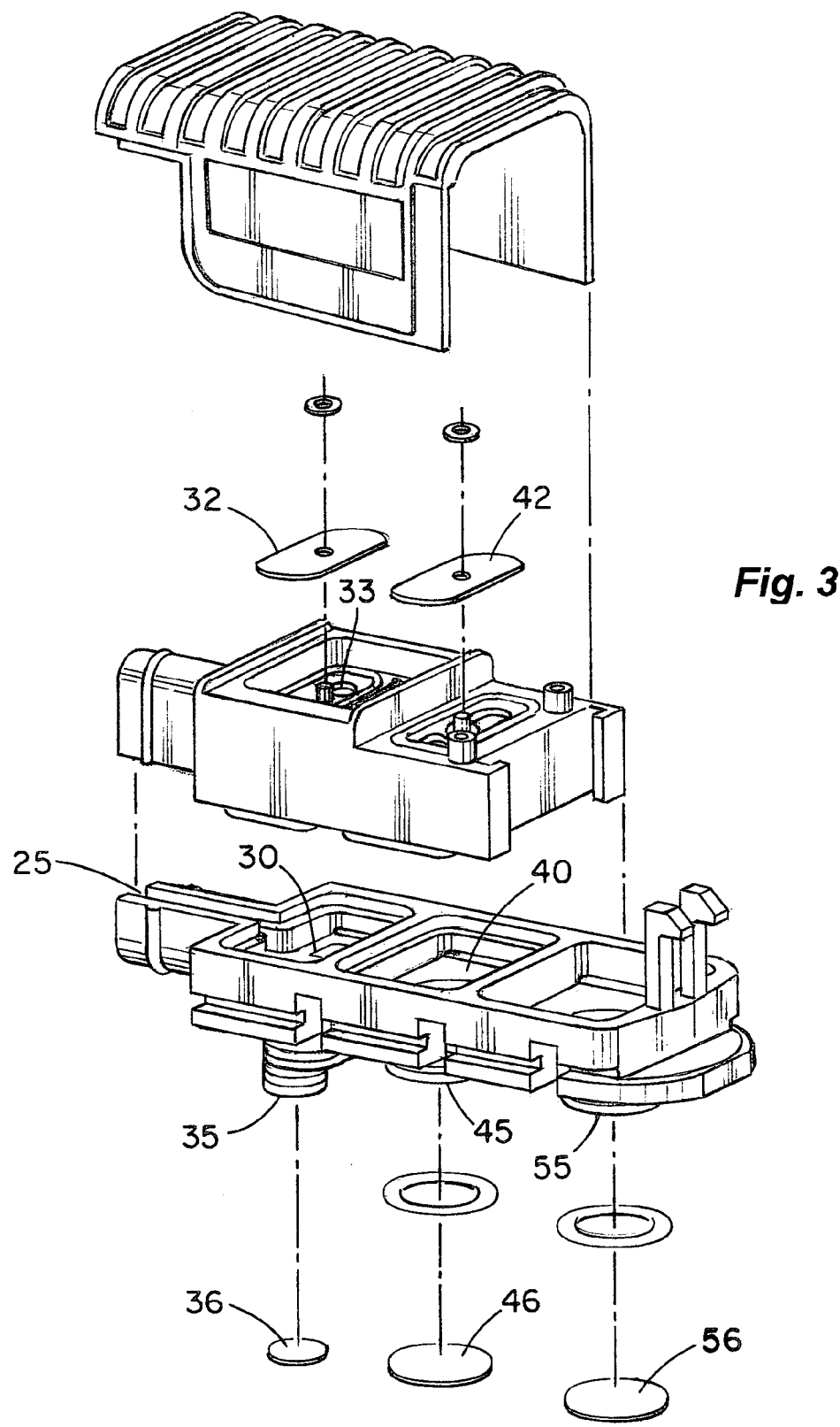
FIG. 3 is an exploded perspective view of the sample chamber assembly 20 corresponding to FIGS. 1 and 2.

The sample chamber assembly 20 is removably attached to the top of the main housing of the testing device 10 by means of a locking wire clip 65 and sample chamber cap 60, as depicted in the exploded view in FIG. 1. The sample chamber cap 60 locks onto prongs on the sample chamber assembly 20 as depicted in FIGS. 1 and 3. A removable medically-clean mouthpiece 70 (shown in FIG. 1) is then placed onto the sample chamber inlet 25 in preparation for use by a testing subject. The sample chamber assembly 20 is easily removed by pressing a 0.5 in. wide blade through the sample chamber cap 60 vents to release the retaining hooks on the top of the main housing of the testing device 10, and thereby allow removal of the sample chamber cap 60 and wire clip 65. Once the wire retaining clip 65 is removed from the sample chamber base, the sample chamber assembly 20 is simply lifted off the main housing of the testing device 10.

FIG. 3 depicts the components that make up the sample chamber assembly 20. FIG. 5 illustrates the air flow through the sample chamber assembly 20. The removable mouthpiece 70 is placed on the inlet 25 of the sample chamber assembly 20. The subject then exhales into the inlet 25. The exhaled breath passes into the inlet chamber 30 and then passes through a fixed outlet or orifice 33 of a known size covered by a one-way flapper valve 32. This provides a pressure buildup within the inlet chamber 30 to allow a series of pressure measurements to be taken by a pressure sensor 14 over time during exhalation. Other types of one-way valves could be substituted.

A processor with data storage can be used to store and analyze readings from the pressure sensor 14 to provide information on the volume of the exhalation to along with other spirometric data. The temperature of the breath sample can also be measured by a temperature sensor 12 shown in FIG. 4. This breath temperature data and spirometric data may be utilized to ensure that a high-quality breath alcohol sample has been acquired and assist in providing test subject identification. It should be noted that other types of sensors could also be included. as needed. Such sensors can be described in general as biometric sensors.

The biometric sensor array 12, 14 is preferably located within the main housing of the testing device 10. These biometric sensors 12, 14 are connected to the inlet chamber 30 in the sample chamber housing 20 via a sensor port 35, shown in FIGS. 3 and 4. The sensor port 35 extends downward into a corresponding opening in the top of the main housing of the testing device 10, as shown in FIG. 1, which leads to the sensor array 12, 14. The sensor port 35 is protected by a hydrophobic membrane 36 to assure that bodily fluids cannot readily escape the inlet chamber 30 and enter the pressure sensor 14 or temperature sensor 12.

Figure 4:
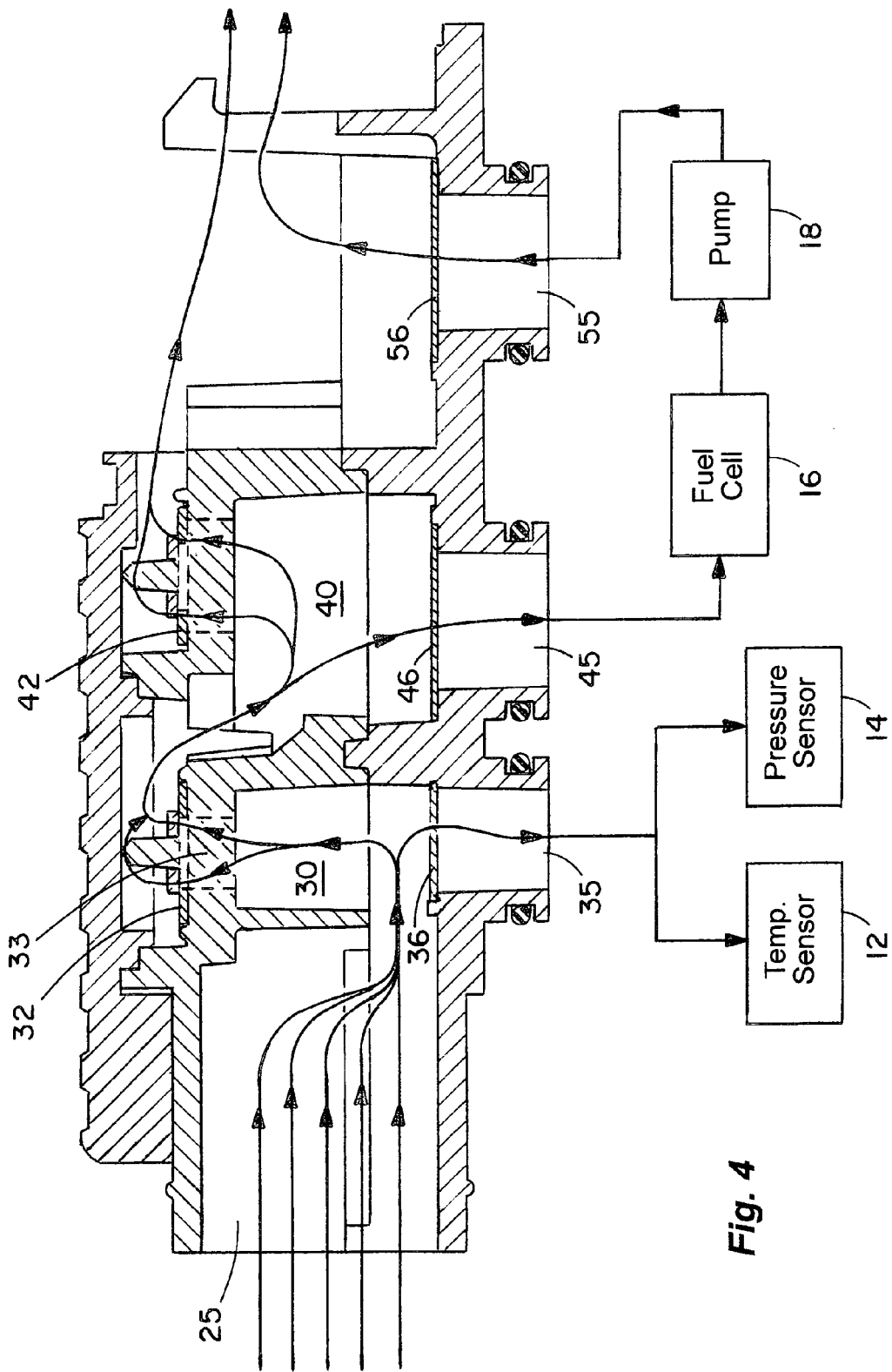
FIG. 4 is a cross-sectional view of the sample chamber assembly 20 showing the flow paths of the breath sample.

Returning to the gas flow path illustrated in FIG. 4, the exhaled breath then travels from the inlet chamber 30 through the outlet 33 and one-way valve 32 into the sample chamber 40. This one-way valve 32 prevents backflow of gas from the sample chamber 40 into the inlet chamber 30. Excess gas in the breath sample is expelled from the sample chamber 40 through an outlet at the top of the sample chamber 40 (e.g., via an orifice with a second one-way flapper valve 42 and the vents in the sample chamber cap 60). The combination of one-way valves 32 and 42 ensure the test subject can only exhale, but not inhale through the sample chamber 40 and dilute the sample with fresh air. Sample dilution is a major problem for many conventional open-tube type mouthpieces.

The combination of one-way valves 32, 42 also ensures that gas from the end-phase of the test subject's breath sample is trapped in the sample chamber 40. This end-phase exhaled gas tends to be from deep within the lungs, and provides a higher-quality breath sample.

The alcohol sensor 16 and sampling pump 18 are located with the main housing of the testing device 10, as previously noted. An alcohol sensor port 45 and an exhaust port 55 extend downward from the bottom of the sample chamber assembly 20, as depicted in FIGS. 3 and 4, and removably insert into corresponding openings in the top of the main housing of the testing device 10 leading to the alcohol sensor 16 and sampling pump 18.

The last step of the sampling process occurs when the pressure drops to zero or ambient pressure levels triggering the sampling pump 18 to pull a predetermined sample from the sample chamber 40 into the alcohol sensor (e.g., fuel cell 16) via the sample chamber port 45. After analysis, the breath alcohol sample is then expelled from the fuel cell 16 through the exhaust port 55 and sample chamber cap 60 ports.

The alcohol sensor port 45 is protected by a second hydrophobic membrane 46 (such as manufactured by Pall Corporation or W. L. Gore & Associates) to ensure that no bodily fluids can escape the sample chamber 40 and enter the alcohol sensor 16 or sampling pump 18. The exhaust port 55 is also protected by a third filter 56 (e.g., a hydrophobic membrane), as shown in FIGS. 3 and 4. Thus, it should be noted that the hydrophobic membranes 36, 46 and 56 prevent bodily fluids and other liquids from escaping the sample chamber assembly 20 and entering the alcohol sensor 16, sensor array 12, 14 or the exhaust port 55. Preferably, all of these ports 35, 45 and 55 form relatively tight seals with their corresponding openings in the main housing, and include O-rings to minimize to possibility of liquids or dirt finding their way into the interior of the testing device 10. The present sample chamber assembly 20 is a significant improvement in the art providing significant strides in user disease prevention, and protecting sensitive sensor arrays from dirt, bodily fluids, water, and tampering while enhancing data acquisition from a breath alcohol sample.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

I claim:

1. A breath alcohol testing device comprising:
  a housing;
  a pressure transducer within the housing;
  an alcohol sensor within the housing; and
  a sample chamber assembly removably attached to the housing having:
  (a) an inlet for receiving a breath sample from a test subject;
  (b) an inlet chamber receiving the breath sample from the inlet and having: (i) a port to the pressure transducer; and (ii) an outlet for the breath sample to flow from the inlet chamber;
  (c) a sample chamber receiving the breath sample from the outlet of the inlet chamber and having a port to the alcohol sensor;
  (d) a filter in the port of the sample chamber preventing liquids from entering the alcohol sensor; and
  (e) a one-way valve in the outlet of the inlet chamber preventing the backflow of gas from the sample chamber into the inlet chamber;
  wherein the outlet and one-way valve of the inlet chamber create back-pressure during the breath sample that is measured by the pressure transducer.

2. The breath alcohol testing device of claim 1 wherein the filter comprises a hydrophobic membrane.

3. The breath alcohol testing device of claim 1 wherein the sample chamber assembly further comprises a filter in the port of the inlet chamber preventing liquids from entering the biometric sensor.

4. The breath alcohol testing device of claim 1 wherein the sample chamber further comprises an outlet with a one-way valve allowing excess gas in the breath sample to escape, and preventing gas from being inhaled by the test subject into the sample chamber.

5. The breath alcohol testing device of claim 1 wherein the sample chamber assembly further comprises an exhaust port for the alcohol sensor with a filter in said exhaust port protecting the alcohol sensor.

6. The breath alcohol testing device of claim 1 further comprising a pump within the housing drawing gas from the breath sample in the sample chamber into the alcohol sensor.

7. A breath alcohol testing device comprising:
  a housing;
  a biometric sensor within the housing;
  an alcohol sensor within the housing; and
  a sample chamber assembly removably attached to the housing having:
  (a) an inlet for receiving a breath sample from a test subject;
  (b) an inlet chamber receiving the breath sample from the inlet and having: (i) a port to the biometric sensor; and (ii) an outlet with a one-way valve allowing the breath sample to flow from the inlet chamber;
  (c) a sample chamber receiving the breath sample from the outlet of the inlet chamber and having: (i) a port to the alcohol sensor; and (ii) an outlet with a one-way valve allowing excess gas in the breath sample to escape from the sample chamber; and
  (d) a filter in the port of the sample chamber preventing liquids from entering the alcohol sensor.

8. The breath alcohol testing device of claim 7 wherein the filter comprises a hydrophobic membrane.

9. The breath alcohol testing device of claim 7 wherein the sample chamber assembly further comprises a filter in the port of the inlet chamber preventing liquids from entering the biometric sensor.

10. The breath alcohol testing device of claim 7 wherein the sample chamber assembly further comprises an exhaust port for the alcohol sensor with a filter protecting the alcohol sensor.

11. The breath alcohol testing device of claim 7 further comprising a pump within the housing drawing gas from the breath sample in the sample chamber into the alcohol sensor.

* * * * *